US00PP30451P3

(12) United States Plant Patent
Lee

(10) Patent No.: US PP30,451 P3
(45) Date of Patent: Apr. 30, 2019

(54) ***ILEX* PLANT NAMED 'MAGDEN'**

(50) Latin Name: *Ilex hybrida*
Varietal Denomination: MAGDEN

(71) Applicant: Robert Edward Lee, Independence, LA (US)

(72) Inventor: Robert Edward Lee, Independence, LA (US)

(73) Assignee: Plant Development Services Inc., Loxley, AL (US)

( * ) Notice: Subject to any disclaimer, the term of this patent is extended or adjusted under 35 U.S.C. 154(b) by 0 days.

(21) Appl. No.: 15/732,122

(22) Filed: Sep. 19, 2017

(65) Prior Publication Data

US 2019/0090401 P1 Mar. 21, 2019

(51) Int. Cl.
*A01H 5/00* (2018.01)

(52) U.S. Cl.
USPC ..... Plt./247

(58) Field of Classification Search
USPC ..... Plt./226, 247
See application file for complete search history.

*Primary Examiner* — Susan McCormick Ewoldt
*Assistant Examiner* — Karen M Redden
(74) *Attorney, Agent, or Firm* — Cassandra Bright

(57) ABSTRACT

A new and distinct *Ilex* cultivar named 'MAGDEN' is disclosed, characterized by stable and distinctive yellow to yellow-green and green variegation. Foliage is distinctively oak leaf shaped. Plant growth is controlled and less vigorous than the parent variety. Plants are very well suited for performance in the landscape, including as a specimen plant or a hedge. The new cultivar is an *Ilex*, suitable for ornamental garden purposes.

2 Drawing Sheets

Latin name of the genus and species: *Ilex hybrida.*
Variety denomination: 'MAGDEN'.

BACKGROUND OF THE INVENTION

The new cultivar is a product of chance discovery by the inventor, at a commercial nursery in Independence, La. during the Summer of 2006. This new variety, hereinafter referred to as 'MAGDEN', was discovered as a naturally occurring, single branch mutation of the parent variety *Ilex* hybrid, 'Magland', U.S. Plant Pat. No. 14,417.

After identifying the new variety as a potentially interesting selection, the inventor first organized propagation of 'MAGDEN' by softwood vegetative cuttings during Fall of 2006 at the same commercial nursery in Independence, La. The inventor continued controlled testing and propagation, assessing stability of the unique characteristics of this variety. Numerous generations have been reproduced and have shown that the unique features of this cultivar are stable and reproduced true to type.

SUMMARY OF THE INVENTION

The cultivar 'MAGDEN' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'MAGDEN' These characteristics in combination distinguish 'MAGDEN' as a new and distinct *Ilex* cultivar:

1. Stable and distinctive Yellow to Yellow-Green and Green variegation.
2. Distinctive oak leaf shaped foliage.
3. Controlled plant growth.

COMPARISON TO PARENT VARIETY

The new variety differs from the parent variety in having a less vigorous plant habit. Additionally, the new variety has a distinctive Yellow and Yellow-Green variegation not seen in the parent variety.

COMMERCIAL COMPARISON

'MAGDEN' can be compared to the commercial variety *Ilex* 'Oak Leaf Red', unpatented. Plants of the new cultivar 'MAGDEN' are similar to plants of 'Oak Leaf Red' in most horticultural characteristics, however, plants of the new cultivar 'MAGDEN' differ in the following:

1. 'MAGDEN' has a less vigorous, more controlled plant habit
2. Foliage of the new variety is distinctively variegated yellow, yellow-green and green, foliage of this comparator is solid green.

'MAGDEN' can be compared to the commercial variety *Ilex* hybrid 'Mary Nell', unpatented. Plants of the new cultivar 'MAGDEN' are similar to plants of 'May Nell' in most horticultural characteristics, however, plants of the new cultivar 'MAGDEN' differ in the following;

1. 'MAGDEN' has smaller, more controlled plant habit
2. Foliage of the new variety is distinctively variegated yellow, yellow-green and green, foliage of this comparator is solid green to grey-green.
3. Foliage of the new variety has a distinctive oak leaf shape, with deep serrations, foliage of this comparator is shallowly serrate.

BRIEF DESCRIPTION OF THE PHOTOGRAPHS

Figure 1:
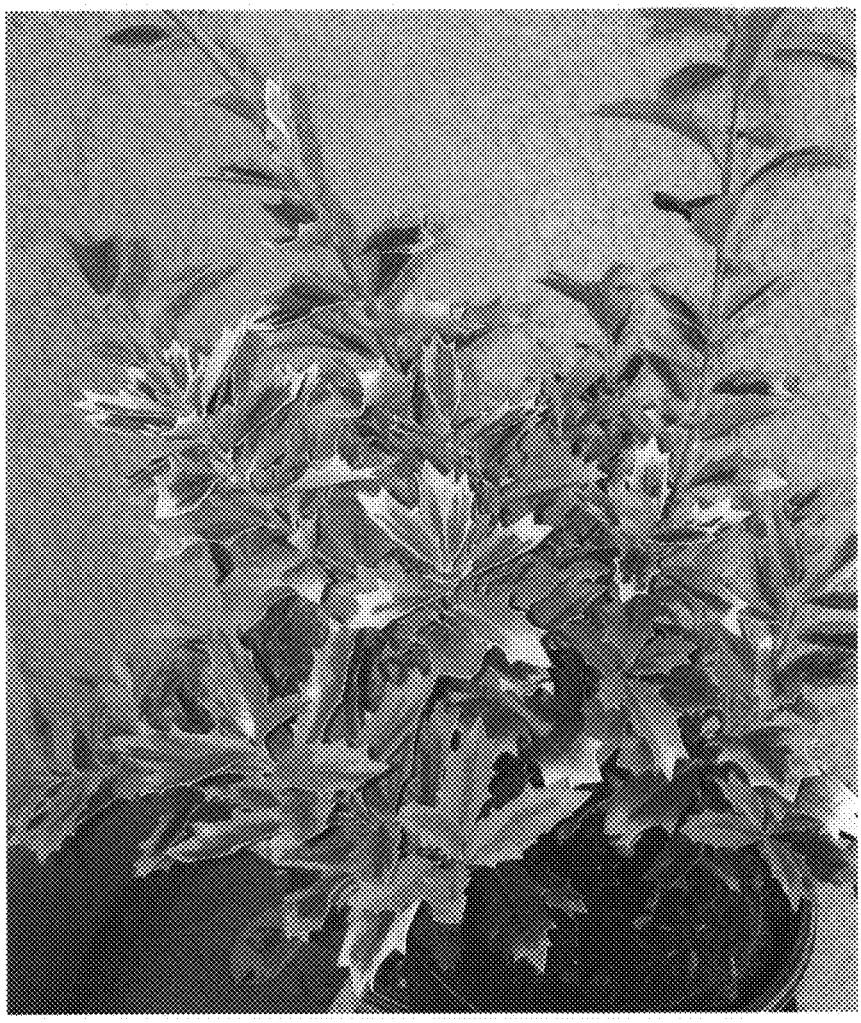

The accompanying photograph in FIG. 1 illustrates in full color a 2 year old plant of the new variety in a 3 gallon pot.

Figure 2:
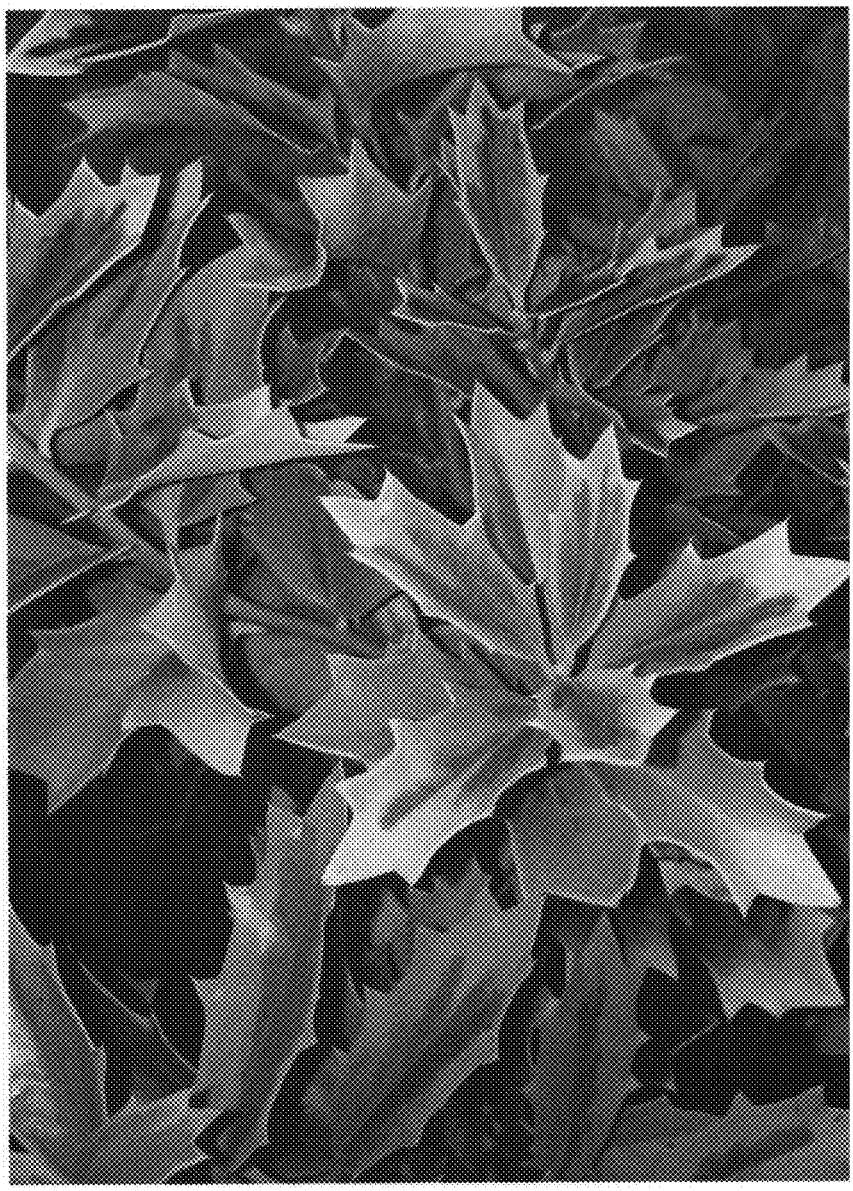

FIG. 2 illustrates a close-up view of the foliage.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'MAGDEN' plants grown outdoors in Loxley, Ala. Plants are approximately 2 years old, in a 3 gallon nursery container. Measurements and numerical values represent averages of typical plant types.

Botanical classification: *Ilex hybrida* 'MAGDEN'.

PROPAGATION

Typically by softwood cuttings in Spring and Summer.

Root description: Very dense fibrous roots. Colored near RHS Grey-Brown 199C. Somewhat shallow rooted.

PLANT

Growth habit: Upright evergreen shrub. Narrow V shape, not quite as narrow as to be columnar.

Height: Approximately 60 cm.

Plant spread: Approximately 36 cm.

Branching characteristics: Moderately well branched, approximately 3 to 6 primary branches from the center of the plant. Branches occur at approximately 15° to 40° angles. Each primary branch has 2 to 3 lateral branches.

Primary branches:

Length of primary branches: Average range 12 to 25 cm, then branching into further laterals.

Diameter of primary branches: Approximately 6 to 1.2 mm.

Primary branch strength: Very strong, difficult to break.

Primary branch color: Oldest wood near RHS Yellow-Green N144A with thin covering of Greyed-Orange 165C and 165D. Immature branches near Green 143C.

Primary branch texture: Glabrous. Oldest wood somewhat rough.

Lateral branches:

Length of lateral branches: Average range 10 to 25 cm.

Diameter of lateral branches: Average 4 mm.

Lateral branch strength: Strong.

Lateral branch color: Near RHS Yellow-Green N144C.

Lateral branch texture: Glabrous, smooth.

Internode length: Average 1.0 to 1.5 mm.

Age of plant described: Approximately 1 year.

FOLIAGE

Leaf:

*Type*.—Simple.

*Arrangement*.—Alternate.

*Average length*.—Approximately 6 to 7 cm.

*Average width*.—Approximately 3 cm.

*Shape of blade*.—Overall oblong. Deep serrations forming an oak-leaf shape.

*Apex*.—Acute with a sharp serration.

*Base*.—Attenuate, coming nearly obtuse with age.

*Attachment*.—Stalked

*Margin*.—Deeply serrate. Typically 6 sharp serrations about 8 mm deep.

*Texture of top surface*.—Glabrous.

*Texture of bottom surface*.—Glabrous.

*Appearance of top surface*.—Glossy.

*Appearance of bottom surface*.—Matte.

*Color*.—Young foliage upper side: Foliage in early Spring may be solid Yellow 2C, or with faint Yellow-Green 144A center blotch. Young foliage under side: Near RHS Yellow-Green 150C with center blotch near 144A. Mature foliage upper side: Margin near Yellow 4B, fading to 2C. Center blotch near Green 143C, surrounded by a halo near Yellow-Green N144C. Mature foliage under side: Thick margin near Yellow-Green 150C, center blotch near 144A, surrounded by Yellow-Green 145B.

*Venation*.—Type: Pinnate. Venation color upper side: Mid-vein near RHS Yellow-Green 150A, lateral veins indistinguishable from leaf blade. Venation color under side: Mid-vein near RHS Yellow-Green 144C, lateral veins indistinguishable from leaf blade.

*Petiole*.—Length: About 3 mm. Diameter: About 2 mm. Color: Upper Surface: Near RHS Yellow-Green 144A. Lower Surface: Near RHS Yellow-Green 144C.

FLOWER

Flowering not observed to date.

OTHER CHARACTERISTICS

Disease and pest resistance: Neither resistance nor susceptibility to normal diseases and pests of *Ilex* observed. Potential insect problems include holly leaf miner, spider mites, whitefly and scale. Potential disease problems include leaf spot, leaf rot, tar spot and powdery mildew.

Temperature tolerance: USDA Zone 6 through 9.

Fruit/seed production: Not observed to date.

What is claimed is:

1. A new and distinct cultivar of *Ilex* plant named 'MAGDEN' as herein illustrated and described.

* * * * *